United States Patent [19]

Okumura et al.

[11] Patent Number: 5,763,702
[45] Date of Patent: Jun. 9, 1998

[54] METHOD FOR PRODUCTION OF BENZENE HALILDE

[75] Inventors: Yasunori Okumura; Osamu Kaieda, both of Ibaraki, Japan

[73] Assignee: Nippon Shokubai Co., Ltd., Osaka-fu, Japan

[21] Appl. No.: 719,778

[22] Filed: Sep. 25, 1996

[30] Foreign Application Priority Data

Sep. 26, 1995 [JP] Japan ................................ 7-248042
Aug. 13, 1996 [JP] Japan ................................ 8-213640

[51] Int. Cl.$^6$ ................................................ C07C 19/08
[52] U.S. Cl. ................................................ 570/142; 570/201
[58] Field of Search ................................ 570/142, 201

[56] References Cited

U.S. PATENT DOCUMENTS

| 2,439,237 | 4/1948 | Cass. | |
| 5,329,054 | 7/1994 | Theriot | 570/142 |

FOREIGN PATENT DOCUMENTS

| 61-12650 | 1/1986 | Japan. | |
| 61-43130 | 1/1986 | Japan. | |
| 6425737 | 1/1989 | Japan. | |
| 2 122 190 | 1/1984 | United Kingdom | 570/142 |
| 2122190 | 5/1993 | United Kingdom. | |

Primary Examiner—Alan Siegel

[57] ABSTRACT

A benzene halide is produced with high purity at a high yield by heating a halogen-substituted benzene carboxylic acid in the presence of a basic catalyst in a solvent.

9 Claims, No Drawings

METHOD FOR PRODUCTION OF BENZENE HALILDE

BACKGROUND OF THE INVENTION

1. Field of the Invention

This invention relates to a method for the production of a benzene halide. The benzene halides which are provided by this invention are useful as an intermediate for medicines, agricultural pesticides, liquid crystals, or polymerization catalysts.

2. Description of the Prior Art

As a means for producing a benzene halide, British Patent No. 2,122,190 discloses a method which effect the production by heating a halogen-substituted benzene carboxylic acid in a solvent, particularly an aprotic polar solvent, to a temperature of not less than 20° C. thereby decarboxylating the carboxylic acid. Though the relevant specification describes the reaction as being performed in dimethyl formamide, it has no mention whatever of such data as yield. The data offered therein indicate that the reaction using such a polar solvent as ethylene glycol demands time for the sake of exalting the yield.

JP-A-64-25,727 discloses a method which implements the decarboxylation of a halogen-substituted benzene carboxylic acid by heating this carboxylic acid in a nitrogen atom-containing organic base which neither contains a hydrogen atom capable of forming direct hydrogen bond with a nitrogen atom nor possesses heterocyclic aromatic attribute or in a mixture of the nitrogen atom-containing organic base with a nonpolar organic solvent. A similar method is disclosed in JP-A-06-65,120. These methods, however, are at a disadvantage economically in necessitating use of an expensive solvent.

JP-A-07-145,083 discloses a method which decarboxylates pentafluorobenzoic acid in an alkanolamine. Since the alkanolamine is in a solid state at room temperature, the reactants are not uniformly dispersed therein in the initial stage of reaction and, therefore, the reaction is not easily controlled.

It is, therefore, an object of this invention to provide a method which enables a benzene halide to be produced with high purity on a commercial scale and in a high yield.

SUMMARY OF THE INVENTION

The object mentioned above is accomplished by the following aspects of this invention.

(1) A method for the production of a benzene halide which comprises heating a halogen-substituted benzene carboxylic acid in the presence of a basic catalyst in a solvent thereby effecting the decarboxylation of the carboxylic acid.

(2) A method according to the aspect (1) mentioned above, wherein the dipole moment of the molecule of the solvent is not less than 1.0.

(3) A method according to the aspect (1) mentioned above, wherein the boiling point of the solvent is not less than 100° C. under normal pressure.

(4) A method according to the aspect (1) mentioned above, wherein an amount of the basic catalyst is in the range of 0.01 to 1 mol per 1 mol of the halogen-substituted benzene carboxylic acid.

(5) A method according to the aspect (1) mentioned above, wherein the basic catalyst is at least one member selected from the group consisting of an alkali metal compound and an alkaline earth metal compound.

(6) A method according to the aspect (1) mentioned above, wherein the halogen-substituted benzene carboxylic acid is added continuously to the reaction system and the benzene halide is extracted continuously from the reaction system during the process of the reaction.

(7) A method according to the aspect (1) mentioned above, wherein the reaction of decarboxylation is carried out in the additional presence of a sulfate catalyst.

(8) A method according to the aspect (7) mentioned above, wherein the sulfate catalyst is one member which is obtained by hydrolyzing a benzene carbonitrile halide with an aqueous sulfuric acid solution and then neutralizing sulfuric acid contained in a halogen-substituted benzene carboxylic acid.

(9) A method according to the aspect (1) mentioned above, which comprises (i) hydrolyzing a benzene carbonitrile halide by using an aqueous sulfuric acid solution to obtain a halogen-substituted benzene carboxylic acid, then (ii) neutralizing sulfuric acid contained in the halogen-substituted carboxylic acid, and further (iii) subjecting the neutralized halogen-substituted carboxylic acid to decarboxylation reaction.

(10) A method according to the aspect (1) mentioned above, wherein the halogen-substituted benzene carboxylic acid is pentafluorobenzoic acid and the benzene halide is pentafluorobenzene.

In the method of production according to this invention, the benzene halide aimed at is obtained with high purity in a high yield on a commercial scale by effecting the decarboxylation of a halogen-substituted benzene carboxylic acid by heating this carboxylic acid in the presence of a basic catalyst in a solvent.

Further, in the method of production according to this invention, since the halogen-substituted benzene carboxylic acid is obtained by hydrolyzing a benzene carbonitrile halide with an aqueous sulfuric acid solution and the halogen-substituted benzene carboxylic acid consequently containing sulfuric acid has the sulfuric acid thereof neutralized prior to the step of the reaction of decarboxylation, the benzene halide aimed at is obtained with high purity in a high yield on a commercial scale by a simple procedure from the halogen-substituted benzene carboxylic acid when the halogen-substituted benzene carboxylic acid is decarboxylated by being heated in the copresence of a basic catalyst and a sulfate catalyst in a solvent.

PREFERRED EMBODIMENT OF THE INVENTION

First, one preferred embodiment (A) of the method for the production of a benzene halide according to the present invention is characterized by implementing the decarboxylation of a halogen-substituted benzene carboxylic acid by heating this carboxylic acid in the presence of a basic catalyst in a solvent.

The halogen-substituted benzene carboxylic acid as the starting material in the method of production according to the embodiment (A) mentioned above does not impose any particular restriction. Appropriately, it is a halogen-substituted benzene carboxylic acid which is represented by the following general formula (I):

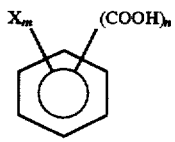 (I)

wherein X represents a halogen atom, providing X is not limited to one species but may be arbitrarily selected from among as many species as is denoted by the symbol m and preferably at least one of X's is a fluorine atom and more preferably all the X's are fluorine atoms, m represents an integer of 1–5, n represents an integer of 1–4, and m and n jointly satisfy the expression, $2 \leq m+n \leq 6$. The benzene halide which is the product of the reaction is not particularly limited. Preferably, it is a benzene halide which is represented by the following general formula (II):

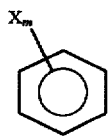 (II)

wherein X represents a halogen atom, providing X is not limited to one species but may be arbitrarily selected from among as many species as is denoted by the symbol m and preferably at least one of X's is a fluorine atom and more preferably all the X's are fluorine atoms, and m represents an integer of 1–5. Typical examples of the halogen-substituted benzene carboxylic acids represented by the general formula (I) mentioned above and typical examples of the benzene halides represented by the general formula (II) mentioned above are shown in Table 1 below. Among them, as the halogen-substituted benzene carboxylic acid, pentafluorobenzoic acid is preferable, and as the benzene halide, pentafluorobenzene is preferable.

TABLE 1

| Starting material (Halogen-substituted benzene carboxylic acid) | Product (Benzene halide) |
| --- | --- |
| Pentafluorobenzoic acid | Pentafluorobenzene |
| 2,3,4,5-Tetrafluorobenzoic acid | 1,2,3,4-Tetrafluorobenzene |
| 2,3,5,6-Tetrafluorobenzoic acid | 1,2,4,5-Tetrafluorobenzene |
| 2,4-Dichloro-5-fluorobenzoic acid | 1,3-Dichloro-4-fluorobenzene |
| 3,4,5-Trifluorobenzoic acid | 1,2,3-Trifluorobenzene |
| 2,3,4-Trifluorobenzoic acid | 1,2,3-Trifluorobenzene |
| 2,3,6-Trifluorobenzoic acid | 1,2,4-Trifluorobenzene |
| 2,4,5-Trifluorobenzoic acid | 1,2,4-Trifluorobenzene |
| 2,4,6-Trifluorobenzoic acid | 1,3,5-Trifluorobenzene |
| 3-Chloro-4-fluorobenzoic acid | 1-Chloro-2-fluorobenzene |
| 2-Chloro-4-fluorobenzoic acid | 1-Chloro-3-fluorobenzene |
| 2-Chloro-6-fluorobenzoic acid | 1-Chloro-3-fluorobenzene |
| 2,3-Difluorobenzoic acid | 1,2-Difluorobenzene |
| 3,4-Difluorobenzoic acid | 1,2-Difluorobenzene |
| 2,4-Difluorobenzoic acid | 1,3-Difluorobenzene |
| 2,6-Difluorobenzoic acid | 1,3-Difluorobenzene |
| 3,5-Difluorobenzoic acid | 1,3-Difluorobenzene |
| 2,5-Difluorobenzoic acid | 1,4-Difluorobenzene |
| 2-Bromobenzoic acid | Bromobenzene |
| 3-Bromobenzoic acid | Bromobenzene |
| 4-Bromobenzoic acid | Bromobenzene |
| 2-Chlorobenzoic acid | Chlorobenzene |
| 3-Chlorobenzoic acid | Chlorobenzene |
| 4-Chlorobenzoic acid | Chlorobenzene |
| 2-Fluorobenzoic acid | Fluorobenzene |
| 3-Fluorobenzoic acid | Fluorobenzene |

TABLE 1-continued

| Starting material (Halogen-substituted benzene carboxylic acid) | Product (Benzene halide) |
| --- | --- |
| 4-Fluorobenzoic acid | Fluorobenzene |
| Tetrafluorophthalic acid | 1,2,3,4-Tetrafluorobenzene |
| Tetrafluoroisophthalic acid | 1,2,3,5-Tetrafluorobenzene |
| 1,4-Difluoropyromellitic acid | 1,4-Difluorobenzene |

The starting material mentioned above is not particularly limited but may be selected from a wide range of compounds produced by methods heretofore known to the art. In the present invention, a method which is an embodiment (C) below mentioned wherein, the compounds which are produced by hydrolyzing benzene carbonitrile halides represented by the following general formula (III):

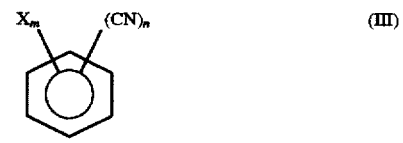 (III)

wherein X represents a halogen atom, providing X is not limited to one species but may be arbitrarily selected from among as many species as is denoted by the symbol m and preferably at least one of X's is a fluorine atom and more preferably all the X's are fluorine atoms, m represents an integer of 1–5, n represents an integer of 1–4, and m and n jointly satisfy the expression, $2 \leq m+n \leq 6$, with an aqueous sulfuric acid solution may be preferably used.

As typical benzene carbonitrile halides, there are pentafluorobenzonitrile, 2,4,6-trifluorobenzonitrile, tetrafluorophthalonitrile, 1,4-difluoropyromelitonitrile and the like. Among these, preferable benzene carbonitrile is pentafluorobenzonitrile.

Appropriately, the solvent to be used in the method of production according to the embodiment (A) mentioned above is a polar solvent, preferably a polar solvent having a dipole moment of the molecule of not less than 1.0, and particularly preferably a polar solvent having a dipole moment of the molecule of not less than 2.0. Though the upper limit of the dipole moment of the molecule is not particularly defined, the dipole moment is properly not more than 6.0. The polar solvent poses no problem so long as it is separable by distillation from the relevant benzene halide. A polar solvent having a boiling point of not less than 100° C. is preferable and a polar solvent having a boiling point of not less than 130° C. is particularly preferable. Though the upper limit of the boiling point poses no problem so long as the solvent is capable of solving the basic catalyst and the halogen-substituted benzene carboxylic acid, the boiling point is preferably not more than 500° C., particularly preferably not more than 300° C.

As typical examples of the solvent which is effectively usable herein, polyhydric alcohols such as ethylene glycol (dipole moment 2.31, boiling point 197.5° C.), ethylene glycol monoethyl ether (dipole moment 2.08, boiling point 135.6° C.), 1,3-propanediol (dipole moment 2.55, boiling point 214.4° C.), diethylene glycol (dipole moment 2.31, boiling point 245.7° C.), diethylene glycol monomethyl ether (dipole moment 1.60, boiling point 194.1° C.), triethylene glycol (dipole moment 5.58, boiling point 288.0° C.), and glycerol (dipole moment 2.56, boiling point 290.0° C.) and alcohol such as 1-butanol (dipole moment 1.75, boiling point 117.7° C.) and 1-octanol (dipole moment 1.76, boiling point 195.2° C.) and water (dipole moment 1.82,boiling point 100° C.) may be cited. Among other solvents cited above, ethylene glycol proves particularly advantageous from the viewpoints of economy and physical properties.

The amount of the solvent to be used appropriately is in the range of 10–2000 parts by weight, preferably in the range of 20–1000 parts by weight, based on 100 parts by weight of the halogen-substituted benzene carboxylic acid. If the amount of the solvent to be used is less than the lower limit of the range mentioned above, the reaction will not be easily controlled. If the amount is more than the upper limit, the productivity of the reaction will be degraded.

As typical examples of the basic catalyst to be effectively used in the method of production according to the embodiment (A) mentioned above, alkali metal compounds such as sodium hydroxide, potassium hydroxide, sodium hydrogencarbonate, potassium hydrogen-carbonate, sodium carbonate, and potassium carbonate and/or alkaline earth metal compounds such as calcium hydroxide, magnesium hydroxide, calcium carbonate, and magnesium carbonate may be cited. Among other basic catalysts cited above, alkaline earth metal compounds prove particularly suitable. In all the basic catalysts mentioned above, it is appropriate to use calcium hydroxide or calcium carbonate from the viewpoints of economy and physical properties. Properly the amount of the basic catalyst to be used is in the range of 0.01–1 mol, preferably 0.05–0.5 mol, based on one mol of the halogen-substituted benzene carboxylic acid. If the amount of the basic catalyst to be used is less than the lower limit of the range mentioned above, the disadvantage ensues that the reaction velocity will be decreased and the productivity will be impaired. If the amount exceeds the upper limit of the range, the disadvantage arises that such secondary reactions as hydroxylation will proceed.

As respects the reaction temperature (the heating condition mentioned above) of the decarboxylation in the method of production according to the embodiment (A) mentioned above, though the reaction generally proceeds at temperatures exceeding 80° C., the reaction temperature properly is in the range of 80°–300° C., preferably in the range of 100°–200° C. If the reaction temperature is higher than the upper limit of the range mentioned above, the reaction will proceed abruptly and permit no easy control. If it is lower than the lower limit, the productivity will be impaired.

The isolation of the benzene halide which is obtained by the method of production according to the embodiment (A) mentioned above can be easily accomplished by distillation. The isolation can be carried out either during or after the reaction, whichever better suits the occasion. The solvent which remains after the isolation of the benzene halide can be recycled through the reaction of decarboxylation contemplated by this invention.

In the method of production according to the embodiment (A) mentioned above, when a solvent separable by distillation from the benzene halide is used, the reaction can be continuously carried out by continuously adding the halogen-substituted benzene carboxylic acid to the reaction system and meanwhile continuously extracting the benzene halide from the reaction system during the course of the reaction. By performing the reaction in the manner described above, it is made possible to prevent the reaction temperature from being gradually lowered by the benzene halide formed during the reaction and enable the reaction temperature to remain constantly at a high level and the reaction to proceed efficiently.

Another embodiment (B) of the method for the production of a benzene halide according to this invention is characterized by performing the decarboxylation in the additional presence of at least one catalyst selected from among sulfates, preferably sulfates of ammonia, alkali metals, or alkaline earth metals. The sulfate catalyst functions as a promoter for the basic catalyst.

The method of production according to the embodiment (B) mentioned above is identical with the method of production according to the embodiment (A) mentioned above except that the former method uses the sulfate catalyst in combination with the basic catalyst mentioned above.

As typical examples of the sulfate catalyst mentioned above, ammonium sulfate, sodium sulfate, potassium sulfate, rubidium sulfate, cesium sulfate, magnesium sulfate, calcium sulfate, strontium sulfate, and barium sulfate may be cited.

Appropriately, the amount of the sulfate catalyst to be used is in the range of 0.001–10 mols, preferably 0.01–1 mol, based on 1 mol of the halogen-substituted benzene carboxylic acid. If the amount of the sulfate catalyst to be used is less than the lower limit of the range mentioned above, the effect of the catalyst will be unduly small. If this amount is larger than the upper limit, the sulfate will remain in a large amount in the reaction system after completion of the reaction and will require an extra work of due treatment.

Yet another embodiment (C) of this invention is characterized by a method, which comprises (i) hydrolyzing a benzene carbonitrile halide by using an aqueous sulfuric acid solution to obtain a halogen-substituted benzene carboxylic acid, then (ii) neutralizing sulfuric acid contained in the halogen-substituted carboxylic acid, and further (iii) subjecting the neutralized halogen-substituted carboxylic acid to decarboxylation reaction. Thus the embodiment (C) makes possible to carry out the decarboxylation reaction in a system using sulfate catalyst similar to other embodiment (B). Owing to this method, the halogen-substituted benzene carboxylic acid as the starting material does not need to be isolated but may be recycled in a form of a reaction liquid containing the sulfate as it is through the decarboxylation.

That is, it becomes possible to use the reaction mixture in the decarboxylation reaction without a step for removing sulfuric acid from the halogen-substituted benzene carboxylic acids thus obtained and a step for drying the halogen-substituted benzene carboxylic acid wherein sulfuric acid is removed.

The reaction of hydrolysis mentioned above is not particularly discriminated on account of the kind of method to be adopted. The hydrolysis can be carried out in an aqueous sulfuric acid solution of a concentration in the range of 30–90% by weight at a temperature in the range of 100°–180° C.

As the sulfate after neutralizing sulfric acid in the embodiment (C) mentioned above, there are sulfates of ammonia, an alkali metal, and an alkaline earth metal, and by-produced ammonium sulfate can also be used.

As typical examples of the basic neutralizer to be used for neutralizing the sulfuric acid, alkali metal compounds such as sodium hydroxide, potassium hydroxide, sodium hydrogencarbonate, potassium hydrogencarbonate, sodium carbonate, and potassium carbonate and/or alkaline earth metal compounds such as calcium hydroxide, magnesium hydroxide, calcium carbonate, and magnesium carbonate may be cited. In the basic neutralizing agents cited above, it is advantageous particularly to use calcium hydroxide or calcium carbonate from the viewpoints of economy and physical properties. Theoretically, the basic neutralizing agent is used in an amount enough for neutralizing the sulfuric acid present in the system. It may be used safely in an amount larger than is necessary for the purpose of the neutralization because it can be used concurrently as a basic catalyst for the reaction of decarboxylation. As a preferred method, there is a method by neutralizing sulfuric acid by adding a equimalar amount of a basic neutralizing agent for sulfuric acid and then subjecting to decarboxylation reaction. In this case, a basic catalyst is added in a necessary amount of decarboxylation. Preferred amount of the basic catalyst is similar to that of the embodiment (A). As typical examples of at least one of the sulfates of ammonia, alkali metal, and alkaline earth metal which are obtained during the neutralization of sulfuric acid, ammonium sulfate, sodium sulfate, potassium sulfate, rubidium sulfate, cesium sulfate, magnesium sulfate, calcium sulfate, strontium sulfate, and barium sulfate may be cited. An amount of sulfate existed after neutralization is similar to that of the embodiment (B).

Now, the method of production according to this invention will be described more specifically below with reference to working examples.

EXAMPLE 1

In a distillation apparatus provided with a stirring devices, 13.90 g (66 m.mols) of pentafluorobenzoic acid, 40 g of ethylene glycol, and 0.82 g (11 m.mols) of calcium hydroxide were placed and heated to 140° C. and the ensuring reaction was continued for 4 hours and pentafluorobenzene formed meanwhile by the reaction was continuously extracted from the apparatus. By the distillation, pentafluorobenzene was obtained in an amount of 10.20 g (61 m.mols), i.e. in a yield of 92.6%. By gas chromatography, the product was found to have purity of not less than 99.0%.

EXAMPLE 2

The reaction solution remaining after the distillation of pentafluorobenzene in Example 1 was cooled to room temperature and 13.90 g (66 m.mols) of pentafluorobenzoic acid was added to the cooled reaction solution. The resultant mixture was then heated to 160° C. and the ensuing reaction was continued for 3 hours and pentafluorobenzene produced meanwhile by the reaction was continuously extracted. By the distillation, pentafluorobenzene was obtained in an amount of 10.52 g (63 m.mols), i.e. in a yield of 95.6%. By gas chromatography, the product was found to have purity of not less than 99.0%.

EXAMPLE 3

In a distillation apparatus provided with a stirring device, 13.90 g (66 m.mols) of pentafluorobenzoic acid, 40 g of ethylene glycol, and 2.50 g (25 m.mols) of calcium carbonate were placed and heated to 120° C. and the ensuring reaction was continued for 8 hours and pentafluorobenzene formed meanwhile by the reaction was continuously extracted from the apparatus. By the distillation, pentafluorobenzene was obtained in an amount of 10.27 g (61 m.mols), i.e. in a yield of 93.2%. By gas chromatography, the product was found to have purity of not less than 99.0%.

EXAMPLE 4

In a distillation apparatus provided with a stirring device, 13.90 g (66 m.mols) of pentafluorobenzoic acid, 40 g of ethylene glycol, and 0.82 g (11 m.mols) of calcium hydroxide were placed and heated to 140° C. and the ensuring reaction was continued and pentafluorobenzene formed meanwhile by the reaction was extracted continuously and such an amount of pentafluorobenzoic acid as corresponded to the number of mols of the extracted pentafluorobenzene was added continuously to the reaction solution. The amount of pentafluorobenzoic acid thus added totalled 10.0 g and the reaction time totalled 6 hours. By the distillation, pentafluorobenzene was obtained in an amount of 17.70 g (106 m.mols), i.e. in a yield of 93.5%. By gas chromatography, the product was found to have purity of not less than 99.0%.

EXAMPLE 5

In a three-necked flask provided with a stirring device, a reflux condenser, and a thermometer, 13.90 g (66 m.mols) of pentafluorobenzoic acid, 40 g of ethylene glycol, and 0.82 g (11 m.mols) of calcium hydroxide were placed and heated and the ensuant reaction was continued for 6 hours, with the reaction temperature gradually lowered meanwhile from the initial level of 140° C. to the terminal level of 110° C. After the reaction was completed, pentafluorobenzene was isolated by distillation. By the distillation, pentafluorobenzene was obtained in an amount of 8.02 g (48 m.mols), i.e. in a yield of 72.8%. By gas chromatography, the product was found to have purity of not less than 99.0%. The solution remaining after the distillation could be recycled through the subsequent cycle of reaction, though the pentafluorobenzoic acid as the starting material remained in the solution.

CONTROL 1

In a distillation apparatus provided with a stirring device, 13.90 g (66 m.mols) of pentafluorobenzoic acid and 0.82 g (11 m.mols) of calcium hydroxide were placed and heated to 140° C. and left reacting for 4 hours. The distillation produced absolutely no pentafluorobenzene and the reaction solution contained absolutely no pentafluorobenzene.

CONTROL 2

In a distillation apparatus provided with a stirring device, 13.90 g (66 m.mols) of pentafluorobenzoic acid and 40 g of ethylene glycol were placed and heated to 140° C. and the ensuant reaction was continued for 7 hours and pentafluorobenzene formed meanwhile by the reaction was continuously extracted from the apparatus. The distillation produced pentafluorobenzene in an amount of 3.56 g (21 m.mols), i.e. in a yield of 32.3%. By gas chromatography, the product was found to have purity of not less than 99.0%.

EXAMPLE 6

In a distillation apparatus provided with a stirring device, 10.00 g (0.057 mol) of 2,4,6-trifluorobenzoic acid, 30 g of ethylene glycol, and 0.50 g (0.0065 mol) of calcium hydroxide were placed and heated to 160° C. and the ensuring reaction was continued for 5 hours and 2,3,5-trifluorobenzene formed meanwhile by the reaction was continuously extracted from the apparatus. By the distillation, 1,3,5-trifluorobenzene was obtained in an amount of 7.13 g (0.054 m.mol), i.e. in a yield of 94.7%. By gas chromatography, the product was found to have purity of not less than 99.0%.

EXAMPLE 7

In a distillation apparatus provided with a stirring device, 10.00 g (0.057 mol) of 2-chloro-6-fluorobenzoic acid, 40 g of 1,3-propanediol, and 0.82 g (0.011 mol) of calcium hydroxide were placed and heated to 170° C. and the ensuring reaction was continued for 6 hours and 1-chloro-3-fluorobenzene formed meanwhile by the reaction was continuously extracted from the apparatus. By the distillation, 1-chloro-3-fluorobenzene was obtained in an amount of 6.95 g (0.053 m.mol), i.e. in a yield of 93.4%. By gas chromatography, the product was found to have purity of not less than 99.0%.

EXAMPLE 8

In a distillation apparatus provided with a stirring device, 10.00 g (0.042 mol) of 3,4,5,6-tetrafluorobenzoic acid, 60 g of diethylene glycol, and 0.85 g (0.011 mol) of calcium hydroxide were placed and heated to 220° C. and the ensuring reaction was continued for 6 hours and 1,2,3,4-tetrafluorobenzene formed meanwhile by the reaction was continuously extracted from the apparatus. By the distillation, 1,2,3,4-tetrafluorobenzene was obtained in an amount of 5.25 g (0.035 m.mol), i.e. in a yield of 83.3%. By gas chromatography, the product was found to have purity of not less than 99.0%.

EXAMPLE 9

In a three-necked flask provided with a stirring device, a thermometer, and a reflux condenser, 50 g (0.26 mol) of pentafluorobenzonitrile and 250 g of an aqueous 65 wt % sulfuric acid solution were placed and refluxed for reaction for 15 hours. The reaction solution was cooled to room temperature and pentafluorobenzoic acid consequently precipitated was separated by means of filtration to obtain 98.0 g of a cake. By analysis, this cake was found to contain 90% by weight of pentafluorobenzoic acid, 5.0% by weight of sulfuric acid, 0.6% by weight of ammonium sulfate, and 2.6% by weight of water. Into 49.0 g of the cake thus obtained, 1.82 g (0.025 mol) of calcium hydroxide was added to neutralize sulfuric acid.

In a distillation apparatus provided with a stirring device, 50.8 g of the cake [containing 44.1 g (0.21 mol) of calcium sulfate obtained by neutralizing sulfuric acid], 150 g of ethylene glycol, and 2.55 g (0.034 mol) of calcium hydroxide as the basic catalyst were placed and heated to 140° C. and the ensuring reaction was continued for 4 hours and pentafluorobenzene formed meanwhile by the reaction was extracted from the apparatus continuously. By the distillation, pentafluorobenzene was obtained in an amount of 33.2 g (0.20 mol), i.e. in a yield of 95.0%. By gas chromatography, the product was found to have purity of not less than 99.0%.

EXAMPLE 10

In a three-necked flask provided with a stirring device, a thermometer, and a reflux condenser, 50 g (0.26 mol) of pentafluorobenzonitrile and 250 g of an aqueous 65 wt % sulfuric acid solution were placed and refluxed for reaction for 15 hours. The reaction solution was cooled to room temperature and pentafluorobenzoic acid consequently precipitated was separated by means of filtration to obtain 98.0 g of a cake. By analysis, this cake was found to contain 90% by weight of pentafluorobenzoic acid, 5.0% by weight of sulfuric acid, 0.6% by weight of ammonium sulfate, and 2.6% by weight of water. Into 49.0 g of a cake thus obtained, 1.0 g (0.025 mol) of sodium hydroxide was added to neutralized sulfuric acid.

In a distillation apparatus provided with a stirring device, 50.0 g of the cake containing sodium sulfate obtained by neutralizing sulfuric acid [containing 44.1 g (0.21 mol) of pentafluorobenzoic acid], 150 g of ethylene glycol, and 0.74 g (0.010 mol) of calcium hydroxide as the basic catalyst were placed and heated to 140° C. and the ensuring reaction was continued for 4 hours and pentafluorobenzene formed meanwhile by the reaction was extracted from the apparatus continuously. By the distillation, pentafluorobenzene was obtained in an amount of 32.9 g (0.20 mol), i.e. in a yield of 94.1%. By gas chromatography, the product was found to have purity of not less than 99.0%.

EXAMPLE 11

A similar method to Example 1 was carried out except that 0.87 g (6.6 mmol) of ammonium sulfate as a catalyst was added in addition to calcium hydroxide. Pentafluorobenzene thus obtained was 10.30 g (62 mmol) and the yield was 93.3%. Purity measured by gas chromatography was not less than 99.0%.

What is claimed is:

1. A method for the production of a benzene halide which comprises heating a halogen-substituted benzene carboxylic acid in the presence of a basic catalyst in a polyhydric alcohol solvent having a dipole moment greater than 1.0 and thereby affecting decarboxylation of said carboxylic acid, wherein said basic catalyst is at least one member selected from the group consisting of an alkali metal compound and an alkaline earth metal compound.

2. A method according to claim 1, wherein the boiling point of said solvent is not less than 100° C. under normal pressure.

3. A. A method according to claim 1, wherein an amount of the basic catalyst is in the range of 0.01 to 1 mol per 1 mol of the halogen-substituted benzene carboxylic acid.

4. A method according to claim 1, wherein said halogen-substituted benzene carboxylic acid is added continuously to the reaction system and said benzene halide is extracted continuously from the reaction system during the process of the reaction.

5. A method according to claim 1, wherein the reaction of decarboxylation is carried out in the additional presence of a sulfate catalyst.

6. A method according to claim 5, wherein said sulfate catalyst is one member which is obtained by hydrolyzing a benzene carbonitrile halide with an aqueous sulfuric acid solution and then neutralizing a sulfate ion contained in a halogen-substituted benzene carboxylic acid.

7. A method according to claim 1, which comprises (i) hydrolyzing a benzene carbonitrile halide by using an aqueous sulfuric acid solution to obtain a halogen-substituted benzene carboxylic acid, then (ii) neutralizing sulfuric acid contained in the halogen-substituted carboxylic acid, and further (iii) subjecting the neutralized halogen-substituted carboxylic acid to decarboxylation reaction.

8. A method according to claim 1, wherein said halogen-substituted benzene carboxylic acid is pentafluorobenzoic acid and said benzene halide is pentafluorobenzene.

9. A method according to claim 1, wherein the reaction is carried out in the range of 100°–200° C.

* * * * *